United States Patent
Kroll

(10) Patent No.: US 7,076,295 B1
(45) Date of Patent: Jul. 11, 2006

(54) AUTOMATIC DEFIBRILLATION SHOCK ENERGY ADJUSTER

(75) Inventor: Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 465 days.

(21) Appl. No.: 09/981,652

(22) Filed: Oct. 17, 2001

(51) Int. Cl.
*A61N 1/18* (2006.01)

(52) U.S. Cl. .......................................... 607/7

(58) Field of Classification Search ............ 607/5, 607/7, 8
See application file for complete search history.

(56) References Cited

U.S. PATENT DOCUMENTS

| | | | |
|---|---|---|---|
| 3,805,795 A | | 4/1974 | Denniston et al. ...... 128/419 D |
| 4,830,006 A | * | 5/1989 | Haluska et al. ................ 607/4 |
| 5,107,850 A | | 4/1992 | Olive ......................... 128/705 |
| 5,554,174 A | * | 9/1996 | Causey, III ..................... 607/5 |
| 5,674,250 A | * | 10/1997 | de Coriolis et al. ............ 607/7 |
| 5,817,132 A | | 10/1998 | Karagueuzian et al. ........ 607/5 |
| 6,628,986 B1 | * | 9/2003 | Mouchawar et al. ........... 607/8 |

FOREIGN PATENT DOCUMENTS

| | | |
|---|---|---|
| EP | 0 607 637 A2 | 12/1993 |
| WO | WO 99/47206 | 9/1999 |

OTHER PUBLICATIONS

Giuseppe Boriani et al., "*Predictors of Atrial Defibrillation Threshold in Internal Cardioversion,*" PACE, vol. 23 (Nov. 2000, Part II), pp. 1898-1901.

* cited by examiner

*Primary Examiner*—Mark Bockelman

(57) ABSTRACT

An implementation of a technology is described herein for automatically adjusting the magnitude of a defibrillation shock of an implantable cardiac therapy devices (ICTDs) to an improved magnitude. With the technology described herein, an ICTD (such as a defibrillator) automatically determines an improved defibrillation shock energy (DFSE) and automatically adjusts the DFSE so that it delivers a rescuing shock at that level. The defibrillator automatically adjusts the DFSE to an improved level based upon historical and present factors. This abstract itself is not intended to limit the scope of this patent. The scope of the present invention is pointed out in the appending claims.

28 Claims, 5 Drawing Sheets

AUTOMATIC DEFIBRILLATION SHOCK ENERGY ADJUSTER

TECHNICAL FIELD

This invention generally concerns a technology for automatically adjusting the magnitude of a defibrillation shock of an implantable cardiac therapy devices (ICTDs) to an improved magnitude.

BACKGROUND

The heart is a remarkable muscle that beats by way of an electrical conduction system. Disease and abnormality in the electrical pathways cause normal sinus rhythm to be disrupted, prompting the heart to beat too slowly, too quickly, or too erratically. This is called a cardiac arrhythmia.

Cardiac Arrhythmia

An arrhythmia occurs when the SA node becomes diseased (sick sinus syndrome), or when the AV node fails to pass an impulse along the heart's electrical pathway, or when there is blockage anywhere in the heart's conduction system. An arrhythmia affects the heart's pumping ability by either speeding up or slowing down the electrical impulses responsible for each heartbeat. If the heart beats too slowly (bradycardia), it will not pump enough blood to meet the body's demands. If the heart beats too quickly (tachycardia), it will not have enough time between contractions to fill completely and will fail to pump enough blood to the body. Sometimes a tachycardia will progress into fibrillation, which is a "quivering" of either the heart's atria or ventricles and an inability to pump at all. Fibrillation, which can also occur spontaneously, causes a serious disruption in the rhythm and function of the heart.

Arrhythmias are further classified according to where they originate: atrial or supraventricular (above the ventricles) arrhythmias and ventricular (in the ventricles) arrhythmias.

Fibrillation

Fibrillation is caused when the heart muscle begins to quiver, or fibrillate, continually and cannot contract normally. When a heart is in a state of fibrillation, there is no synchronization between the atria and the ventricles. This causes the patient to experience a racing sensation—and sometimes discomfort in the chest—and/or to feel lightheaded or faint.

Atrial Fibrillation (AF)

Atrial fibrillation (AF or AFib) is a very fast, uncontrolled atrial heart rate caused by rapidly fired signals. During an episode of AF, the atrial heart rate may exceed 350 beats per minute. Not all of these beats reach the ventricles, so the ventricular rate is not this high. However, the ventricular rate is often higher than normal, exceeding 100 beats per minute. Sometimes an impulse will circle the atria, triggering atrial flutter, which is similar to AF. Alone, AF is rarely serious, but if a patient has high blood pressure, valvular disease, or heart muscle damage, AF can increase the risk of stroke or heart failure.

There are several treatments for AF, including medication and electrical cardioversion. Electrical cardioversion converts the heart rate back to normal sinus rhythm through the use of a controlled electrical shock that excites all the heart cells at once, allowing the SA node to resume its role as the heart's natural pacemaker.

Ventricular Fibrillation (VF)

Ventricular fibrillation (VF or VFib) is a chaotic heart rate resulting from multiple areas of the ventricles attempting to control the heart's rhythm. Ventricular fibrillation can occur spontaneously (generally caused by heart disease) or when ventricular tachycardia has persisted too long. When the ventricles fibrillate, they cannot contract normally, hence, they cannot effectively pump blood. The instant VF begins, effective blood pumping stops. VF quickly becomes more erratic, resulting in cardiac arrest or sudden cardiac death. This arrhythmia must be corrected immediately via a shock from an external defibrillator. The defibrillator stops the chaotic electrical activity and restores normal sinus rhythm.

Treatment of Arrhythmias

There are several techniques that physicians use to detect cardiac arrhythmias and, in particular, fibrillations. There are also several treatment options for rhythm management. One such treatment option is the implantation of an implantable cardiac stimulation device (ICSD), such as a pacemaker or implantable cardioverter-defibrillator (ICD).

Implantable Cardiac Therapy Devices (ICTDs)

Pacemakers and ICDs (and other implantable cardiac stimulation device (ICSDs) are common examples of implantable cardiac therapy devices (ICTDs).

Implantable cardiac therapy devices (ICTDs) are implanted within the body of a patient to monitor, regulate, and/or correct heart function. ICTDs include implantable cardiac stimulation devices (e.g., implantable cardiac pacemakers, implantable defibrillators) that apply stimulation therapy to the heart as well as implantable cardiac monitors that monitor heart activity.

ICTDs typically include a control unit positioned within a casing that is implanted into the body and a set of leads that are positioned to impart stimulation and/or monitor heart activity. With improved processor and memory technologies, the control units have become increasingly more sophisticated, allowing them to monitor many types of conditions and apply tailored stimulation therapies in response to those conditions.

ICTDs are typically capable of being programmed remotely by an external programming device, often called a "programmer". Today, individual ICTDs are equipped with telemetry circuits that communicate with the programmer. One type of programmer utilizes an electromagnetic wand that is placed near the implanted cardiac device to communicate with the implanted device. The wand contains a coil that forms a transformer coupling with the ICTD telemetry circuitry. The wand transmits low frequency signals by varying coil impedance.

Treatments with ICTDs

Depending upon the type and severity of the arrhythmia, physicians may choose from a number of therapies to manage the abnormal rhythm. Those therapies may include the use of an ICTD.

Cardiac Pacemaker

An artificial permanent pacemaker can take the place of a diseased sinus node or it can help the heart beat despite a blockage in the electrical conduction system. One or more leads (a thin, coated wire) are inserted through a vein, and the tip of the lead (called the electrode) is placed in either the atrium or the ventricle, against, or attached to, the heart's lining. The pulse generator, which encases the electronic circuitry of the pacemaker, is attached to the lead and placed just under the skin, usually in the chest.

Implantable Cardioverter Defibrillator

An implantable cardioverter defibrillator ("defibrillator") is a device much like a pacemaker, with leads and a pulse generator that encloses electronic circuitry. The defibrillator consists of a hybrid (electronic circuitry) and a battery, both of which are enclosed in a sealed titanium capsule. The defibrillator serves as the "brain" of the implanted system, monitoring the heart's activity and generating therapy when appropriate. Defibrillators are high-tech devices that contain sophisticated detection algorithms (to ensure therapy is appropriate and that patients do not receive unnecessary shocks) and tiered therapy options.

Typically, a defibrillator corrects dangerous ventricular arrhythmias which, if left untreated, would result in sudden cardiac death. The device monitors the heart's rhythm and, when it detects a serious fast ventricular arrhythmia, typically administers one of three therapies: pacing (a burst of critically timed low-energy output pulses), cardioversion (low-level shocks delivered at a specific point of the tachyarrhythmia), and/or defibrillation (high-energy shock therapy).

The defibrillator detects fibrillation and delivers electrical therapy-pacing pulses and/or defibrillation therapy. Defibrillator therapy is often prescribed for patients who have generally experienced at least one episode of ventricular tachycardia or ventricular fibrillation, previous cardiac arrest, or drug therapy that was ineffective in controlling the tachyarrhythmia or that caused severe side effects.

Although defibrillators are traditionally and most frequently used to rescue a patient suffering from ventricular fibrillation (VF), some defibrillators are designed to correct atrial fibrillation (AF). AF is typically not fatal; therefore, defibrillation may be delayed. Although an ICTD may rescue AF automatically, most often AF rescue is controlled manual. When a patient recognizes that they suffer from AF, they initiate the AF defibrillation to correct their heart's arrhythmia.

Determination of Defibrillation Shock Energy (DFSE)

After a defibrillator is implanted, it is programmed and tested to ensure the system will effectively correct the patient's arrhythmia. When a defibrillator is implanted into a patient, the medical personal attempt to determine the sufficient shock level (i.e., "sufficient energy level") to effectively correct the patient's arrhythmia (i.e., rescue the patient). This sufficient shock level is also called the defibrillation shock energy (DFSE).

For each patient in a given situation, their heart has a defibrillation threshold (DFT) characteristic. The DFT is the minimum sufficient shock necessary to successfully rescue the patient.

Hopefully, the therapy provided by the defibrillator at the DFSE level is at or above the DFT of the patient. If so, the therapy will rescue the patient. Therefore, it is desirable for the DFSE to be set above and near the DFT of the patient.

A defibrillator may be programmed with more than one defibrillation shock energy (DFSE) setting. More specifically, there may be one or more ventricular fibrillation DFSE (VF-DFSE) settings and one or more atrial fibrillation DFSE (AF-DFSE) settings. Herein, the general term DFSE, without modification or other context, expressly includes the specific terms AF-DFSE and VF-DFSE.

Similarly, a patient has one or more ventricular fibrillation DFT (VF-DFT) and one or more atrial fibrillation DFT (AF-DFT). Herein, the general term DFT, without modification or other context, expressly includes the specific terms AF-DFT and VF-DFT.

The DFSE may be described in energy level units (e.g., measured in voltage or joules) delivered to the patient. Herein, the DFSE for a specific patient is the set at an energy level that is sufficiently high enough to effectively rescue the patient with a high degree of probability.

For example, in one patient, the VF-DFT may be 5 J (joules) and 200 V (volts), but for another, it may be 20 J or 600 V. A typical range for AF-DFT is about 2–5 J. The DFT range may be large across a patient population. Many variables (including the patient, pharmacological, and lead placement) account for this large range. Consequently, the DFT varies with each person and current conditions.

For example, variables related to a particular fibrillation episode may play a role in the DFT. In one study (Boriani, Biffi, et al., *Predictors of Atrial Defibrillation Threshold in Internal Cardioversion*, PACE, Vol. 23 (Nov. 2000)), it was suggested that the DFT for a patient suffering from AF was related to many factors associated with the AF episode itself. Two of the primary factors included duration of the AF episode and the rate of the AF.

FIGS. 1A and 1B are charts derived from the above-referenced study. Theses charts illustrate the relationship between these two primary factors on the AF-DFT. FIG. 1A illustrates that the magnitude of the shock necessary to rescue the AF patient increases with the rate of AF cycles of their AF episode. Similarly, FIG. 1B illustrates that the magnitude of the shock necessary to rescue the DFT AF patient increases with the duration of the AF episode (measured in months in this instance).

Optimum DFSE

The optimum DFSE is the smallest amplitude of energy of a defibrillating shock necessary to rescue the patient with a high degree of probability. An improved DFSE is one that approaches the optimum DFSE and may be equivalent to the optimum DFSE. Of course, there may be many of the factors that go into a determination of an improved or optimum level.

Conventional DFSE Determination

Unfortunately, conventional determination of VF-DFSE and AF-DFSE does not attempt to find an improved level. Typically, a defibrillator is programmed to deliver a series of shocks with increasing, but fixed, energy levels. Of course, the defibrillator only delivers as many shocks as is necessary in that series to rescue the patient.

No conventional defibrillator exists that automatically adjusts the DFSE to an improved level based upon historical and present factors. No conventional defibrillator exists that automatically adjusts the AF-DFSE to an improved level based upon historical and present factors (in particular, present fibrillation episode variables). No conventional defibrillator exists that automatically adjusts the VF-DFSE to an improved level based upon historical and present factors.

Accordingly, there is a need for such a defibrillator.

SUMMARY

Described herein is a technology for automatically adjusting the magnitude of a defibrillation shock of an implantable cardiac therapy device (ICTD) to an improved magnitude. With the technology described herein, an ICTD (such as a defibrillator) automatically determines an improved defibrillation shock energy (DFSE) and automatically adjusts the DFSE so that it delivers a rescuing shock at that level. The defibrillator automatically adjusts the DFSE to an improved level based upon historical and present factors.

With the technology described herein, an ICTD automatically adjusts the atrial fibrillation defibrillation shock energy (AF-DFSE) to an improved level based upon historical and present factors (in particular, present fibrillation episode variables). With the technology described herein, an ICTD automatically adjusts the ventricular fibrillation defibrillation shock energy (VF-DFSE) to an improved level based upon historical and present factors (in particular, present fibrillation episode variables).

This summary itself is not intended to limit the scope of this patent. Moreover, the title of this patent is not intended to limit the scope of this patent. For a better understanding of the present invention, please see the following detailed description and appending claims, taken in conjunction with the accompanying drawings. The scope of the present invention is pointed out in the appending claims.

BRIEF DESCRIPTION OF THE DRAWINGS

Generally, the same numbers are used throughout the drawings to reference like elements and features. Further features and advantages of the claimed embodiments can be more readily understood by reference to the following description taken in conjunction with the accompanying drawings.

DETAILED DESCRIPTION

In the following description, for purposes of the explanation, specific numbers, materials and configurations are set forth in order to provide a thorough understanding of the present invention. However, it will be apparent to one skilled in the art that the present invention may be practiced without the specific exemplary details. In other instances, well-known features are omitted or simplified to clarify the description of the exemplary implementations of present invention, thereby better explain the present invention. Furthermore, for ease of understanding, certain method steps are delineated as separate steps; however, these separately delineated steps should not be construed as necessarily order dependent in their performance.

The following description sets forth one or more exemplary implementations of an Automatic Defibrillation Shock Energy Adjuster that incorporate elements recited in the appended claims. These implementations are described with specificity in order to meet statutory written description, enablement, and best-mode requirements. However, the description itself is not intended to limit the scope of this patent.

The inventor intends these exemplary implementations to be examples. The inventor does not intend these exemplary implementations to limit the scope of the present invention. Rather, the inventor has contemplated that the present invention might also be embodied and implemented in other ways, in conjunction with other present or future technologies.

An example of an embodiment of the Automatic Defibrillation Shock Energy Adjuster may be referred to as an "exemplary DFSE adjuster."

INTRODUCTION

Figure 2:
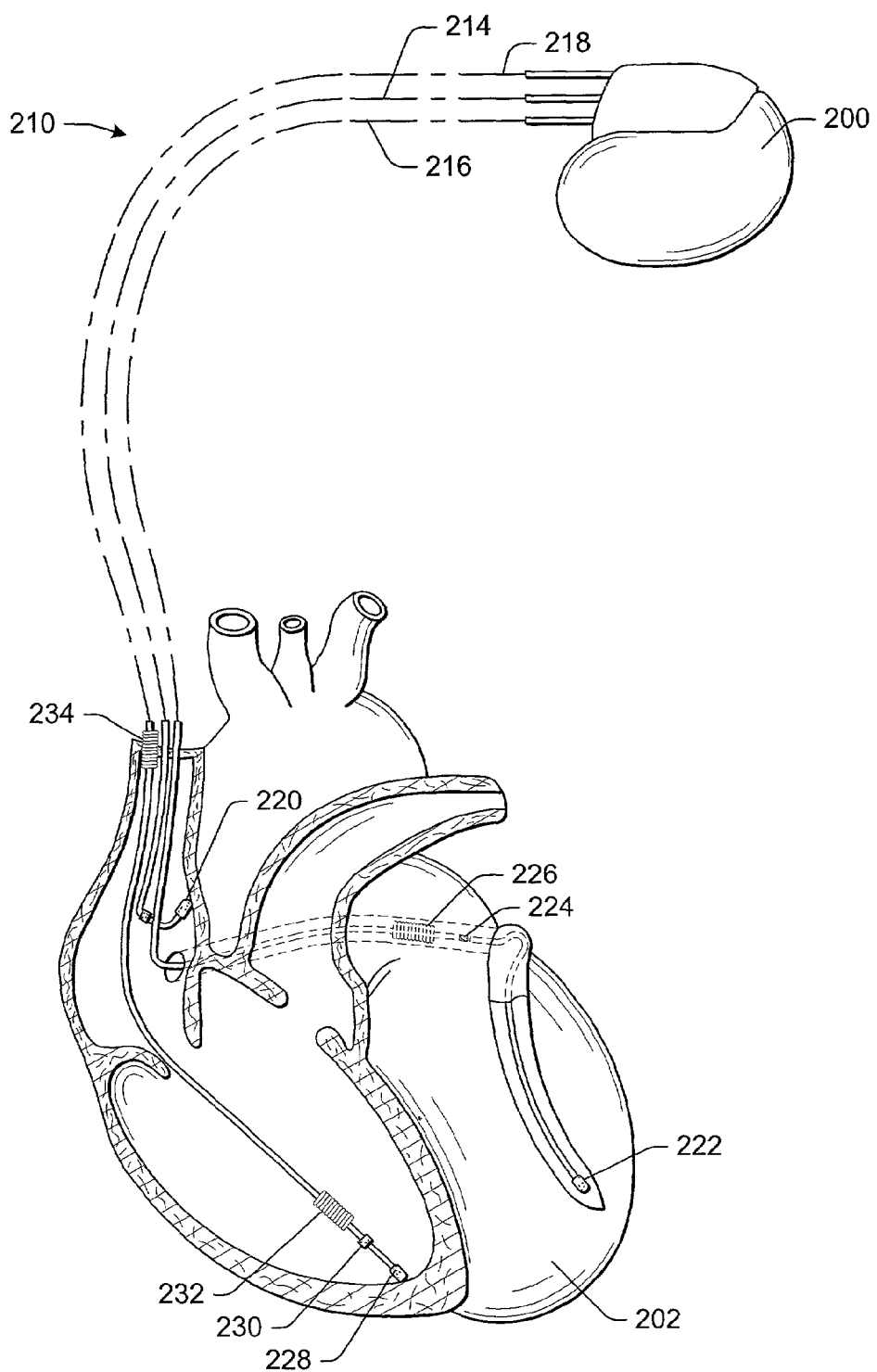
FIG. 2 is a simplified diagram illustrating an implantable cardiac therapy device (ICTD) in electrical communication with at least three leads implanted into a patient's heart for delivering multi-chamber stimulation and shock therapy.
Figure 3:
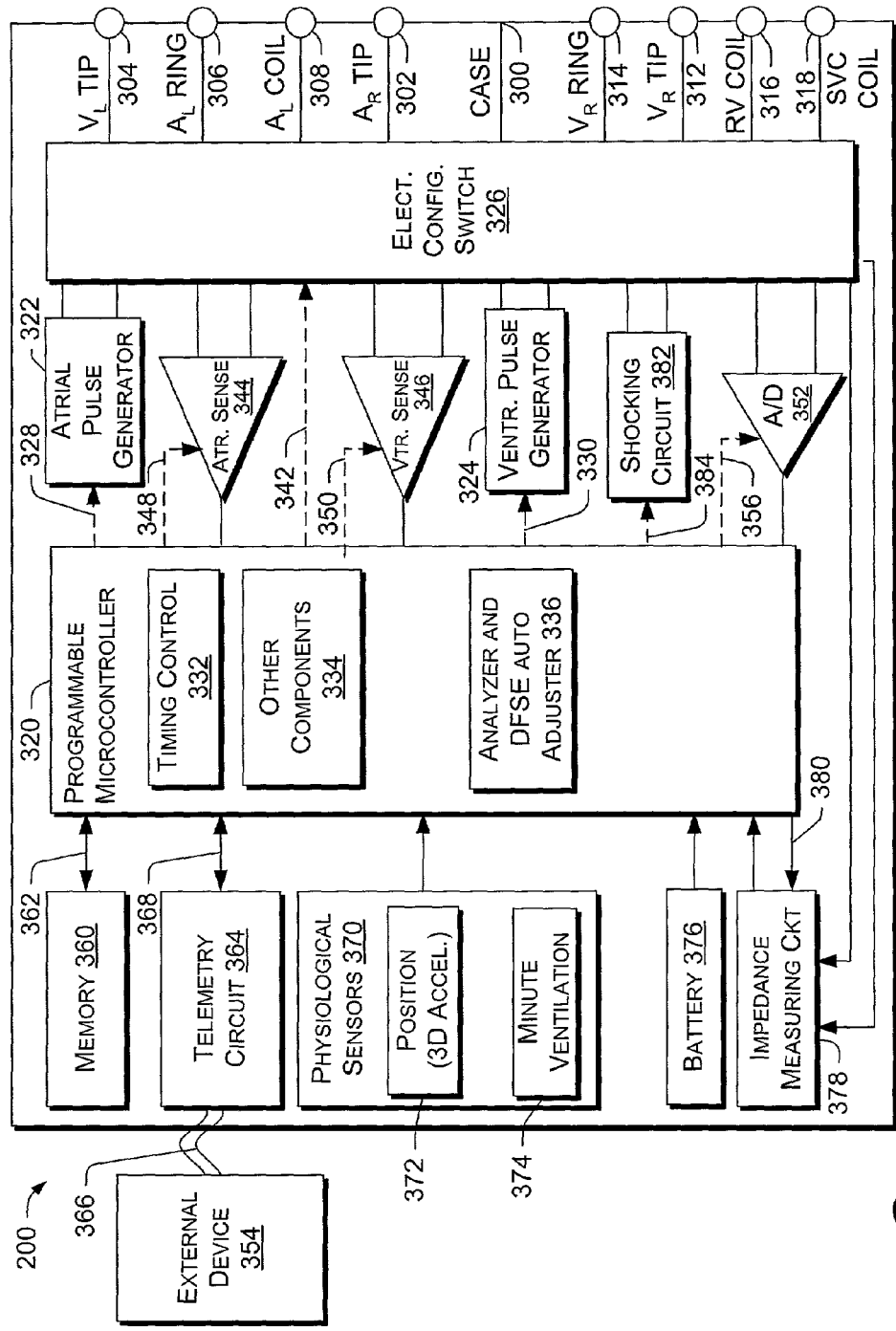
FIG. 3 is a functional block diagram of a multi-chamber implantable cardiac therapy device (ICTD) illustrating the basic elements of a ICTD which can provide cardioversion, defibrillation and pacing stimulation in four chambers of the heart. This is also an example of an ICTD capable of implementing an illustrative embodiment (wholly or partially).

The one or more exemplary implementations, described herein, of the present invention may be implemented (in whole or in part) by an ICTD 200 like that shown in FIGS. 2 and 3.

Generally speaking, the exemplary DFSE adjuster is an ICTD (like ICTD 200) or part of such an ICTD. It automatically adjust the defibrillation shock energy (DFSE) based upon historical and/or present data. In particular, the exemplary DFSE adjuster automatically sets the DFSE for atrial fibrillation (AF) based upon historical data (such as that obtained about prior defibrillation attempts) and based upon present data (such as present AF rate and AF duration). However, the exemplary DFSE adjuster may also be used to automatically set the DFSE for ventricular fibrillation (VF) based upon historical data (such as that obtained about prior defibrillation attempts) and based upon present data (such as present cardiac information).

Unlike the conventional approaches, the exemplary DFSE adjuster automatically adjusts the DFSE. With this, there is no need to return to the office of the medical staff for reprogramming of the ICTD to adjust the DFSE. Furthermore, such manual adjustments are inadequate because they fail to take into account the specific historical and present factors involved during a spontaneous fibrillation.

The exemplary DFSE adjuster automatically adjusts the shock amplitude as closely as possible to the minimum necessary to defibrillate the patient with a high degree of probability. The adjustment is based upon historical data and present data.

The exemplary DFSE adjuster tracks therapy history and learns based upon empirical data of the history. The device automatically adjusts therapy accordingly.

Optimum DFSE

The optimum DFSE is the smallest amplitude of energy of a defibrillating shock necessary to rescue the patient with a high degree of probability. Typically, it will be a close approximation of the defibrillation threshold (DFT) of the patient. An improved DFSE is one that approaches the optimum DFSE and may be equivalent to the optimum DFSE. Of course, there may be many of the factors that go into a determination of an improved or optimum level.

The following are examples of several general factors that go into the determination of an improved or optimum DFSE for a patient:

A. probability of successful rescue (preferably, on first attempt);

B. urgency of immediate rescue;

C. patient variables physical, pharmacological, temporal, etc.);

D. fibrillation episode variables;

E. avoiding inducement of other complications;

F. minimizing the pain of the rescue;

G. maximizing battery life by minimizing number of unsuccessful shocks and minimizing energy drain per shock.

When determining an improved or optimum VF-DFSE, factors A and B (probability of success and urgency) are typically paramount in importance. Unless treated immediately, VF is often fatal. A patient suffering from VF may not survive unless she is rescued with an immediate shock having a high-probability of success. Of course, the other factors (C-G) play a role in determining the an improved or optimum VF-DFSE, but they typically are not as important as the first two factors are.

Optimum AF-DFSE

Patients tend to suffer from AF more frequently than VF. Typically, AF is not directly life threatening. However, there is a link between AF and heart failure.

Regardless, patients may endure AF episode for long periods (potentially, measured in days, months, and years). Often, the patient initiates an atrial defibrillation. Therefore, factor B (i.e., urgency of immediate rescue) is not as important in an improved or optimum AF-DFSE determination. However, the other factors may play a role in determining an improved or optimum AF-DFSE.

Although it would be beneficial to use an improved or optimum DFSE level for both AF and VF, it is of particular value to AF. Since AF is not life threatening, patients may choose to avoid defibrillation (and its associated pain) and endure AF (including its associated increased risk of heart failure).

The shock is painful. It is generally accepted that any shock over 2 J is painful. A typical AF rescue shock is 2–6 J.

While there are numerous ways to reduce the pain of the shock, one very important way is to reduce the energy level of the shock. This unfortunately brings up another problem which is the increase in risk of the shock being unsuccessful which leads to the necessity of a second shock. Clinical testing has shown that patients perceive the second shock as far more upsetting and painful than the first shock.

Figure 1A:
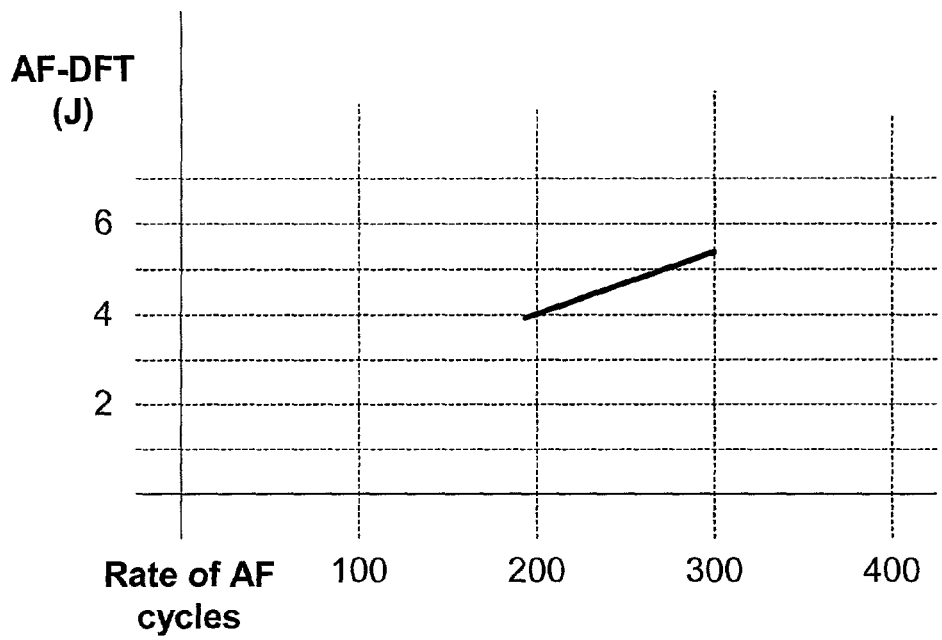
FIGS. 1A and 1B are charts illustrating relationships between variables associated with an AF episode and the AF-DFT.
Figure 1B:
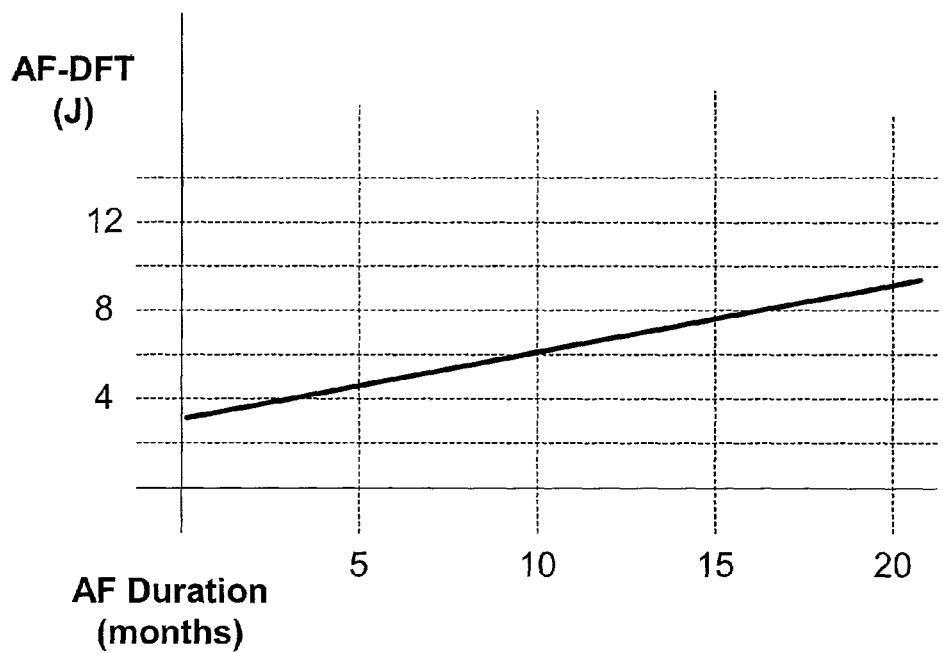

As indicated by FIGS. 1A and 1B, more energy may be needed when AF rate is high. Also, more energy may be needed the longer the heart remains in AF. Aggressiveness of the therapy may be increased when AF is fast. Aggressiveness may also be increased as the AF duration increases.

Exemplary Implantable Cardiac Therapy Device (ICTD)

The techniques that are described below are intended to be implemented in connection with an implantable cardiac therapy system (or a portion thereof). The system includes a ICTD that is configured or configurable to stimulate or shock a patient's heart.

FIG. 2 shows an exemplary ICTD 200 in electrical communication with a patient's heart 202 by way of one or more leads 210 (e.g., leads 214, 216 and 218), suitable for delivering multi-chamber stimulation and shock therapy. To sense atrial cardiac signals and to provide right atrial chamber stimulation therapy, ICTD 200 is coupled to an implantable right atrial lead 214 having at least an atrial tip electrode 220, which typically is implanted in the patient's right atrial appendage. The right atrial lead can also have a ring electrode 234 positioned above the atrial tip electrode 220.

To sense left atrial and ventricular cardiac signals and to provide left chamber pacing therapy, ICTD 200 is coupled to a "coronary sinus" lead 216 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 216 is designed to receive atrial and ventricular cardiac signals and to deliver left ventricular pacing therapy using at least a left ventricular tip electrode 222, left atrial pacing therapy using at least a left atrial ring electrode 224, and shocking therapy using at least a left atrial coil electrode 226.

ICTD 200 is also shown in electrical communication with the patient's heart 202 by way of an implantable right ventricular lead 218 having, in this embodiment, a right ventricular tip electrode 228, a right ventricular ring electrode 230, a right ventricular (RV) coil electrode 232, and an SVC coil electrode 234. Typically, the right ventricular lead 218 is transvenously inserted into the heart 202 so as to place the right ventricular tip electrode 228 in the right ventricular apex so that the RV coil electrode will be positioned in the right ventricle and the SVC coil electrode 234 will be positioned in the superior vena cava. Accordingly, the right ventricular lead 218 is capable of receiving cardiac signals, and delivering stimulation in the form of pacing and shock therapy to the right ventricle.

FIG. 3 shows an exemplary, simplified block diagram depicting various components of ICTD 200. The ICTD can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the inventive techniques and methods described below can be implemented in connection with any suitably configured or configurable ICTD. Accordingly, one of skill in the art could readily duplicate, eliminate or disable the appropriate circuitry in any desired combination to provide a device capable of treating the appropriate chamber(s) with cardioversion, defibrillation and pacing stimulation.

Housing 300 for ICTD 200 is often referred to as the "can", "case" or "case electrode", and may be programmably selected to act as the return electrode for all "unipolar" modes. There may be multiple electrodes positioned on or otherwise supported by the housing. The multiple electrodes can be used for impedance measurements. Housing 300 may further be used as a return electrode alone or in combination with one or more of the coil electrodes, 226, 232 and 234, for shocking purposes. Housing 300 further includes a connector (not shown) having a plurality of terminals 302, 304, 306, 308, 312, 314, 316, and 318 (shown schematically and, for convenience, the names of the electrodes to which they are connected are shown next to the terminals). As such, to achieve right atrial sensing and pacing, the connector includes at least a right atrial tip terminal (AR TIP) 302 adapted for connection to the atrial tip electrode 220.

To achieve left chamber sensing, pacing and shocking, the connector includes at least a left ventricular tip terminal (VL TIP) 304, a left atrial ring terminal (AL RING) 306, and a left atrial shocking terminal (AL COIL) 308, which are adapted for connection to the left ventricular ring electrode 222, the left atrial tip electrode 224, and the left atrial coil electrode 226, respectively.

To support right chamber sensing, pacing and shocking, the connector further includes a right ventricular tip terminal (VR TIP) 312, a right ventricular ring terminal (VR RING)

314, a right ventricular shocking terminal (RV COIL) 316, and an SVC shocking terminal (SVC COIL) 318, which are adapted for connection to the right ventricular tip electrode 228, right ventricular ring electrode 230, the RV coil electrode 232, and the SVC coil electrode 234, respectively.

At the core of the ICTD 200 is a programmable microcontroller 320 which controls the various modes of stimulation therapy. As is well known in the art, microcontroller 320 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 320 includes the ability to process or monitor input signals (data) as controlled by a program code stored in a designated block of memory. The details of the design and operation of the microcontroller 320 are not critical to the described embodiments. Rather, any suitable microcontroller 320 may be used that carries out the functions described herein. The use of microprocessor-based control circuits for performing timing and data analysis functions are well known in the art.

FIG. 3 also shows an atrial pulse generator 322 and a ventricular pulse generator 324 which generate pacing stimulation pulses for delivery by the right atrial lead 214, the right ventricular lead 218, and/or the coronary sinus lead 216 via an electrode configuration switch 326. It is understood that in order to provide stimulation therapy in each of the four chambers of the heart, the atrial and ventricular pulse generators, 322 and 324, may include dedicated, independent pulse generators, multiplexed pulse generators, or shared pulse generators. The pulse generators, 322 and 322, are controlled by the microcontroller 320 via appropriate control signals, 328 and 330, respectively, to trigger or inhibit the stimulation pulses.

Microcontroller 320 further includes timing control circuitry 332 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 may further includes other components 334, such as an arrhythmia detector, a morphology detector, orthostatic compensator, multiphasic stimulation pulse module, evoked response monitor, and/or a minute ventilation (MV) response module. These components can be utilized by the ICTD 200 for determining desirable times to administer various therapies. The other components may be implemented in hardware as part of the microcontroller 320, or as software/firmware instructions programmed into the device and executed on the microcontroller 320 during certain modes of operation.

Microcontroller 320 further includes an analyzer and DFSE auto adjuster 336 that can be utilized by the ICTD 200 for estimating the appropriate DFSE for a patient. Below, the analyzer/adjuster is described further in relation to FIG. 4.

A switch 326 includes a plurality of switches for connecting the desired electrodes to the appropriate I/O circuits, thereby providing complete electrode programmability. Accordingly, switch 326, in response to a control signal 342 from the microcontroller 320, determines the polarity of the stimulation pulses (e.g., unipolar, bipolar, combipolar, etc.) by selectively closing the appropriate combination of switches (not shown). Switch 326 is also used by the evoked response monitor to change an electrode configuration that is utilized for measuring the evoked response.

Atrial sensing circuits 344 and ventricular sensing circuits 346 may also be selectively coupled to the right atrial lead 214, coronary sinus lead 216, and the right ventricular lead 218, through the switch 326 for detecting the presence of cardiac activity in each of the four chambers of the heart. Accordingly, the atrial (ATR. SENSE) and ventricular (VTR. SENSE) sensing circuits, 344 and 346, may include dedicated sense amplifiers, multiplexed amplifiers, or shared amplifiers. Switch 326 determines the "sensing polarity" of the cardiac signal by selectively closing the appropriate switches, as is also known in the art. In this way, the clinician may program the sensing polarity independent of the stimulation polarity.

Each sensing circuit, 344 and 346, preferably employs one or more low power, precision amplifiers with programmable gain and/or automatic gain control, bandpass filtering, and a threshold detection circuit, as known in the art, to selectively sense the cardiac signal of interest. The automatic gain control enables the device 200 to deal effectively with the difficult problem of sensing the low amplitude signal characteristics of atrial or ventricular fibrillation.

The outputs of the atrial and ventricular sensing circuit, 344 and 346, are connected to the microcontroller 320 which, in turn, are able to trigger or inhibit the atrial and ventricular pulse generators, 322 and 324, respectively, in a demand fashion in response to the absence or presence of cardiac activity in the appropriate chambers of the heart. The sensing circuit, 344 and 346, in turn, receive control signals over signal lines, 348 and 350, from the microcontroller 320 for purposes of controlling the gain, threshold, polarization charge removal circuitry (not shown), and the timing of any blocking circuitry (not shown) coupled to the inputs of the sensing circuits, 344 and 346, as is known in the art.

For arrhythmia detection, the device 200 utilizes the atrial and ventricular sensing circuits, 344 and 346, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 320 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 352. The data acquisition system 352 is configured to acquire intracardiac electrogram signals, convert the raw analog data into a digital signal, and store the digital signals for later processing and/or telemetric transmission to an external device 354. The data acquisition system 352 is coupled to the right atrial lead 214, the coronary sinus lead 216, and the right ventricular lead 218 through the switch 326 to sample cardiac signals across any pair of desired electrodes.

Advantageously, the data acquisition system 352 may be coupled to the microcontroller, or other detection circuitry, for detecting an evoked response from the heart 202 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 320 detects a depolarization signal during a window following a stimulation pulse, the presence of which indicates that capture has occurred. The microcontroller 320 enables capture detection by triggering the ventricular pulse generator 324 to generate a stimulation pulse, starting a capture detection window using the timing control circuitry 332 within the microcontroller 320, and enabling the data acquisition system 352 via control signal 356 to sample the cardiac signal that falls in the capture detection window and, based on the amplitude, determines if capture has occurred.

Capture detection may occur on a beat-by-beat basis or on a sampled basis. A capture threshold search can desirably be performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The microcontroller 320 is further coupled to a memory 360 by a suitable data/address bus 362, wherein the programmable operating parameters used by the microcontroller 320 are stored and modified, as required, in order to customize the operation of the ICTD 200 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 202 within each respective tier of therapy. One feature of the described embodiments is the ability to sense and store a relatively large amount of data (e.g., from the data acquisition system 352), which data may then be used for subsequent analysis to guide the programming of the device.

Advantageously, the operating parameters of the implantable device 200 may be non-invasively programmed into the memory 360 through a telemetry circuit 364 in telemetric communication with the external device 354, such as a programmer, transtelephonic transceiver, a wand, or a diagnostic system analyzer. The telemetry circuit 364 is activated by the microcontroller by a control signal 368. The telemetry circuit 364 advantageously allows intracardiac electrograms and status information relating to the operation of the device 200 (as contained in the microcontroller 320 or memory 360) to be sent to the external device 354 through an established communication link 366.

The ICTD 200 can further include a physiologic sensor 370, commonly referred to as a "rate-responsive" sensor because it is typically used to adjust pacing stimulation rate according to the exercise state of the patient. However, the physiological sensor 370 may further be used to detect changes in cardiac output, changes in the physiological condition of the heart, or diurnal changes in activity (e.g., detecting sleep and wake states). Accordingly, the microcontroller 320 responds by adjusting the various pacing parameters (such as rate, AV Delay, V-V Delay, etc.) at which the atrial and ventricular pulse generators, 322 and 324, generate stimulation pulses. While shown as being included within the ICTD 200, it is to be understood that the physiologic sensor 370 may also be external to the ICTD 200, yet still be implanted within or carried by the patient. A common type of rate responsive sensor is an activity sensor, such as an accelerometer (e.g. a three-dimensional accelerometer 372) or a piezoelectric crystal, which is mounted within the housing 300 of the ICTD 200. Other types of physiologic sensors are also known, for example, sensors which sense the oxygen content of blood, respiration rate, and/or minute ventilation, pH of blood, ventricular gradient, etc. (E.g., minute ventilation sensor 374) However, any sensor may be used which is capable of sensing a physiological parameter which corresponds to the exercise state of the patient. The type of sensor used is not critical to the described embodiments and is shown only for completeness.

The described embodiments can utilize a "sleep state" or diurnal sensor that can detect sleep, rest, and wake states. One such sensor is known as "activity variance" wherein an activity sensor is monitored diurnally to detect the low variance in the measurement corresponding to the sleep state.

The ICTD additionally includes a battery 376 that provides operating power to all of the circuits shown in FIG. 2. For the ICTD 200, which employs shocking therapy, the battery 376 is capable of operating at low current drains for long periods of time (e.g. preferably less than 10 µA), and is capable of providing high-current pulses (for capacitor charging) when the patient requires a shock pulse (e.g. preferably, in excess of 2 A, at voltages above 2 V, for periods of 10 seconds or more). The battery 376 also desirably has a predictable discharge characteristic so that elective replacement time can be detected. Accordingly, the device 200 preferably employs lithium/silver vanadium oxide batteries, as is true for most (if not all) current devices.

The ICTD 200 can further include magnet detection circuitry (not shown), coupled to the microcontroller 320. It is the purpose of the magnet detection circuitry to detect when a magnet is placed over the ICTD 200, which magnet may be used by a clinician to perform various test functions of the ICTD 200 and/or to signal the microcontroller 320 that the external device 354 is in place to receive or transmit data to the microcontroller 320 through the telemetry circuits 364.

FIG. 3 also shows an impedance measuring circuit 378 which is enabled by the microcontroller 320 via a control signal 380. Uses for an impedance measuring circuit 378 can include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. In the embodiments described below, the impedance measuring circuit 378 is additionally used to ascertain when a particular electrode configuration that is used for ascertaining an evoked response is no longer able to reliably function in this capacity.

In the case where the ICTD 200 is intended to operate as an implantable cardioverter/defibrillator (ICTD) device, it detects the occurrence of an arrhythmia, and automatically applies an appropriate electrical shock therapy to the heart aimed at terminating the detected arrhythmia. To this end, the microcontroller 320 further controls a shocking circuit 382 by way of a control signal 384. The shocking circuit 382 generates shocking pulses of low (up to 0.5 joule), moderate (0.5–10 joule), or high energy (11 to 40 joule), as controlled by the microcontroller 320. Such shocking pulses are applied to the patients heart 202 through at least two shocking electrodes, and as shown in this embodiment, selected from the left atrial coil electrode 226, the RV coil electrode 232, and/or the SVC coil electrode 234. As noted above, the housing 300 may act as an active electrode in combination with the RV electrode 232, or as part of a split electrical vector using the SVC coil electrode 234 or the left atrial coil electrode 226 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joule), delivered asynchronously (since R-waves may be too disorganized), and pertaining exclusively to the treatment of fibrillation. Accordingly, the microcontroller 320 is capable of controlling the synchronous or asynchronous delivery of the shocking pulses.

Exemplary DFSE Adjuster

Figure 4:
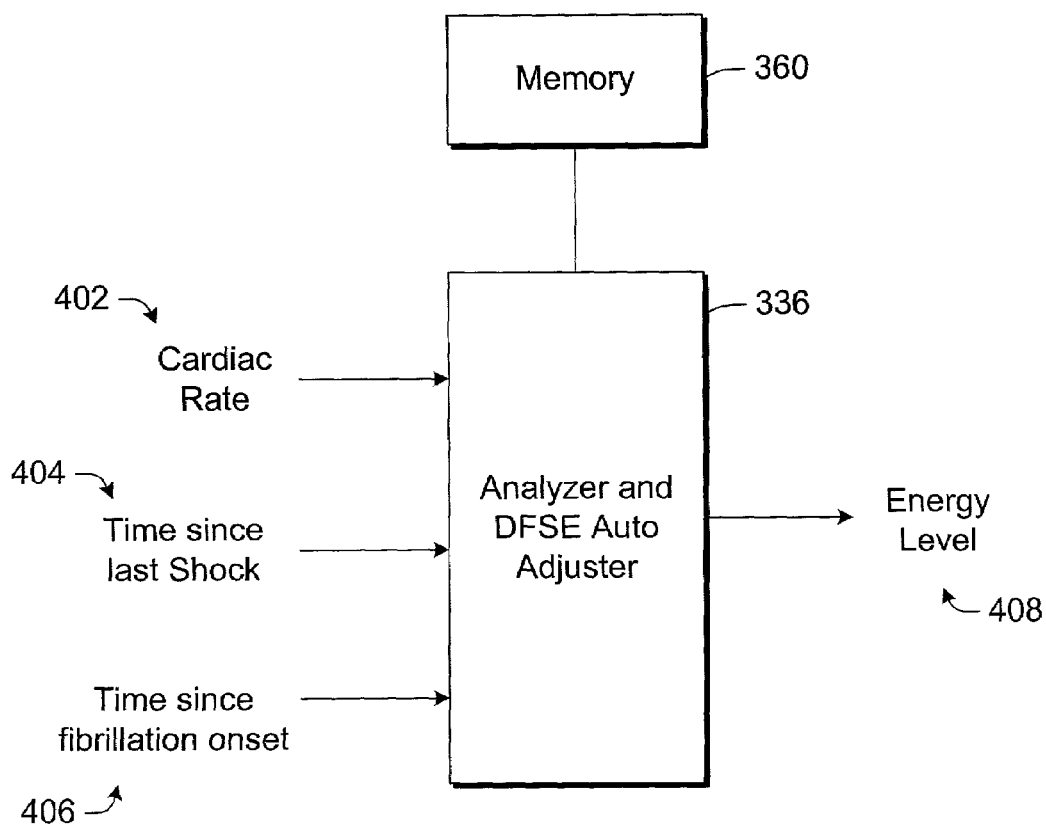
FIG. 4 is a functional block diagram of a portion of an example of an implantable cardiac therapy device (ICTD) capable of implementing an illustrative embodiment (wholly or partially).

FIG. 4 illustrates a functional aspect of the exemplary DFSE adjuster. More particularly, it illustrates the analyzer and DFSE auto adjuster 336 of the ICTD 200. It shows that it is coupled to the memory 360. It may retrieve historical patient-specific data from the memory. Alternatively, it may retrieve from memory 360 generic data gathered during clinical tests or the like. Such data may be stored in memory 360 before installation or transferred by an external programmer or the like. On the left of the analyzer/adjuster 336 of FIG. 4 are inputs of patient-specific data (e.g., sensed data and timing related data). On the right is the output of the analyzer/adjuster 336. The output 408 is a signal corresponding to the adjusted energy level of the DFSE, which is then used by device 200 to deliver the appropriate shock.

With the exemplary DFSE adjuster, the rate 402 is put into automatic DFSE adjustment calculation. The adjustment may be based upon a specific, empirically determined correlation between rate and DFT. This empirical determination may be based on the patient's own personal therapy history (as stored in memory 360) or such history of a patient population that also may be stored in memory 360. Alternatively, this may be accomplished via heuristics, fuzzy logic, an associations table, equation, or any other suitable manner.

Similarly, the time since last shock 404 may also influence the DFSE adjustment. Generally, it is thought that there is a U-shaped correlation in that AF that has suddenly reoccurred after a long absence and also AF that has immediately returned after a recent shock (or was not converted by that shock) will require an increase in energy while events between these two extremes will typically require relatively less energy.

The time since fibrillation onset 406 may also be a determinate. The longer the fibrillation is allowed to proceed, more energy will typically be required to shock it. One option is to immediately deliver a shock upon detection of fibrillation. However, that is not always desirable for two reasons. First, one would like to wait to see if the AF might actually go away on its own. Secondly, one does not like to shock AF if a ventricular rate is high as this can increase the risk of inducement of ventricular fibrillation.

The exemplary DFSE adjuster may employ a neural net from each shock experience for or by building statistical models based on the correlations between the threshold and the input parameters.

Methodological Implementations of the Exemplary DFSE Adjuster

Figure 5:
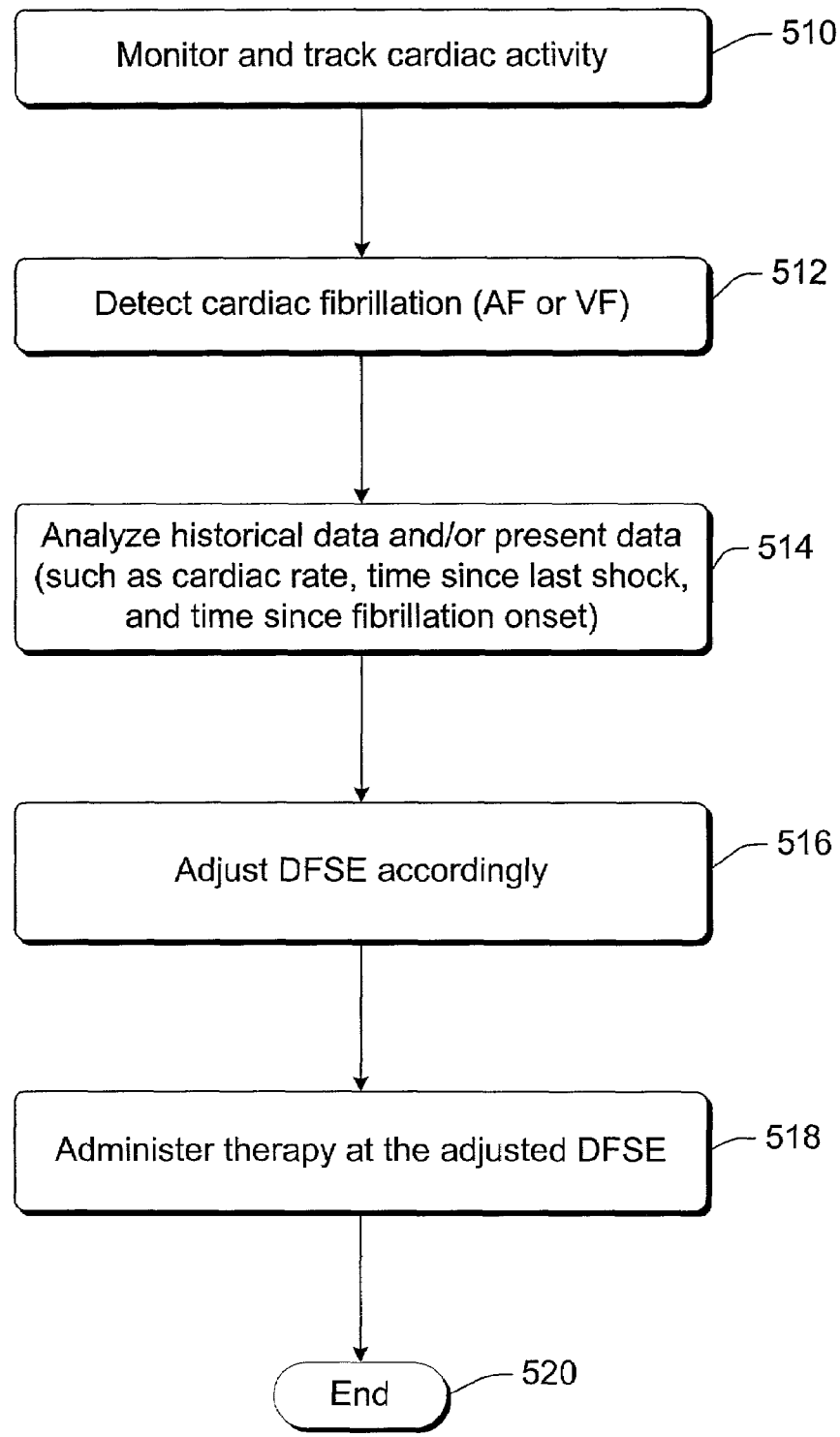
FIG. 5 is a flow diagram that describes a methodological implementation in accordance with one embodiment.

FIG. 5 shows a methodological implementation of the exemplary DFSE adjuster performed by the ICTD 200 (or some portion thereof). This methodological implementation may be performed in software, hardware, or a combination thereof.

At 510 of FIG. 5, the exemplary DFSE adjuster monitors and tracks cardiac activity. This includes cardiac activity during and after delivery of a therapeutic shock. For example, the time since last shock is monitored. In addition, patient-specific data may be stored based on effective shocks and non-effective shocks, such as energy levels, rate, and the like.

At 512, it detects the occurrence of a fibrillation episode. It may be AF or VF.

At 514, adjuster 336 analyzes historical and present data. Historical data may include, for example, time since fibrillation onset and time since last shock as well as either patient-specific historical data or generic data (stored in memory 360), as described above. Present data may include, for example, time since fibrillation onset and cardiac rate. As described above, DFSE increases with cardiac rate and with fibrillation duration, while there is a U-shaped relationship between the time since last shock and the DFSE. For example, the equation may be based on one or more of cardiac rate, time since last shock, and fibrillation duration.

At 516, adjuster 336 adjusts DFSE accordingly. Such adjustments may be calculation based upon empirical data of the specific patient and/or a patient population.

At 518, device 200 administers therapy at the adjusted DFSE. Alternatively, the adjusted DFSE data may be stored in memory 360. At 520, the process ends.

CONCLUSION

Although the invention has been described in language specific to structural features and/or methodological steps, it is to be understood that the invention defined in the appended claims is not necessarily limited to the specific features or steps described. Rather, the specific features and steps are disclosed as preferred forms of implementing the invention.

The invention claimed is:

1. A method for determining an improved defibrillation shock energy (DFSE) for a patient, the method comprising:
   monitoring and tracking cardiac data of a patient by an implantable cardiac therapy device (ICTD);
   analyzing such cardiac data by the ICTD;
   automatically adjusting the DFSE from a first level predetermined to correspond to a first cardiac data value to a second level predetermined to correspond to a second, different, cardiac data value so that the ICTD may deliver a therapeutic shock at an energy level approximating an improved DFSE for the patient;
   wherein the cardiac data comprises data selected from a group consisting of cardiac rate, cardiac fibrillation rate, and duration since last therapeutic shock;
   wherein the duration since last therapeutic shock comprises a first DFSE for fibrillation immediately returning after a recent shock and a fibrillation returning after a long absence and further comprises a second DFSE for fibrillation returning between the two extremes; and
   wherein the first DFSE is higher than the second DFSE.

2. A method as recited in claim 1 further comprising:
    detecting a cardiac fibrillation;
    administering a therapeutic shock to the heart of the patient at the adjusted DFSE set by the adjusting.
3. A method as recited in claim 1 further comprising:
    detecting a cardiac atrial fibrillation (AF);
    administering a therapeutic shock to an atrium of the patient at the adjusted DFSE set by the adjusting.
4. A method as recited in claim 1 further comprising:
    detecting a cardiac ventricular fibrillation (VF);
    administering a therapeutic shock to a ventricle of the patient at the adjusted DFSE set by the adjusting.
5. A method as recited in claim 1, wherein the improved DFSE for the patient approximately corresponds with a defibrillation threshold (DFT) of the patient.
6. A method as recited in claim 1, wherein the improved DFSE for the patient approximately corresponds with an optimum DFSE of the patient.
7. A method as recited in claim 1, wherein the magnitude of the therapeutic shock is adjusted based on U-shaped correlation with the duration since last therapeutic shock.
8. An ICTD comprising circuitry that performs the method as recited in claim 1.
9. An ICTD comprising a computer-readable medium having computer-executable instructions that, when executed by a computer, performs the method as recited in claim 1.
10. A computer-readable medium having computer-executable instructions that, when executed by a computer, performs the method as recited in claim 1.
11. A method as recited in claim 1, wherein the magnitude of the therapeutic shock is a linear function of the cardiac fibrillation rate.
12. A method as recited in claim 1, wherein the magnitude of the therapeutic shock linearly increases with time since fibrillation onset.
13. A method for determining an improved atrial fibrillation defibrillation shock energy (AF-DFSE) for a patient, the method comprising:
    monitoring and tracking cardiac data of a patient by an implantable cardiac therapy devices (ICTDs), wherein such data comprises atrial activity data;
    analyzing such cardiac data by the ICTD;
    automatically adjusting the AF-DFSE from a first level predetermined to correspond to a first cardiac data value to a second level predetermined to correspond to a second, different, cardiac data value so that the ICTD may deliver a therapeutic shock at an energy level approximating an improved AF-DFSE for the patient;
    wherein the cardiac data comprises data selected from a group consisting of cardiac rate, cardiac fibrillation rate, and duration since last therapeutic shock;
    wherein the duration since last therapeutic shock comprises a first AF-DFSE for fibrillation immediately returning after a recent shock and a fibrillation returning after a long absence and further comprises a second AF-DFSE for fibrillation returning between the two extremes; and
    wherein the first AF-DFSE is higher than the second AF-DFSE.
14. A method as recited in claim 13, wherein the improved AF-DFSE for the patient approximately corresponds with an optimum AF-DFSE of the patient.
15. An ICTD comprising circuitry that performs the method as recited in claim 13.
16. A computer-readable medium having computer-executable instructions that, when executed by a computer, performs the method as recited in claim 13.
17. A method as recited in claim 13 further comprising:
    detecting a cardiac atrial fibrillation (AF);
    administering a therapeutic shock to an atria of the patient at the adjusted AF-DFSE set by the adjusting.
18. A method as recited in claim 13, wherein the magnitude of the therapeutic shock is a linear function of the cardiac fibrillation rate.
19. A method as recited in claim 13, wherein the magnitude of the therapeutic shock linearly increases with time since fibrillation onset.
20. A method as recited in claim 13, wherein the magnitude of the therapeutic shock is adjusted based on U-shaped correlation with the duration since last therapeutic shock.
21. A method for determining an improved ventricular defibrillation shock energy (VF-DFSE) for a patient, the method comprising:
    monitoring and tracking cardiac data of a patient by an implantable cardiac therapy device (ICTD), wherein such data comprises ventricle activity data;
    analyzing such cardiac data by the ICTD;
    automatically adjusting the VF-DFSE from a first level predetermined to correspond to a first cardiac data value to a second level predetermined to correspond to a second, different, cardiac data value so that the ICTD may deliver a therapeutic shock at an energy level approximating an Improved VF-DFSE for the patient;
    wherein the cardiac data comprises data selected from a group consisting of cardiac rate, cardiac fibrillation rate, and duration since last therapeutic shock;
    wherein the duration since last therapeutic shock comprises a first VF-DFSE for fibrillation immediately returning after a recent shock and a fibrillation returning after a long absence and further comprises a second VF-DFSE for fibrillation returning between the two extremes; and
    wherein the first VF-DFSE is higher than the second VF-DFSE.
22. A method as recited in claim 21 further comprising:
    detecting a cardiac ventricular fibrillation (VF);
    administering a therapeutic shock to an ventricle of the patient at the adjusted VF-DFSE set by the adjusting.
23. A method as recited in claim 21, wherein the improved VF-DFSE for the patient approximately corresponds with an optimum VF-DFSE of the patient.
24. An ICTD comprising circuitry that performs the method as recited in claim 21.
25. A computer-readable medium having computer-executable instructions that, when executed by a computer, performs the method as recited in claim 21.
26. A method as recited in claim 21, wherein the magnitude of the therapeutic shock varies linearly with the cardiac fibrillation rate.
27. A method as recited in claim 21, wherein the magnitude of the therapeutic shock varies linearly with time since fibrillation onset.
28. A method as recited in claim 21, wherein the magnitude of the therapeutic shock is adjusted based on U-shaped correlation with the duration since last therapeutic shock.

* * * * *